United States Patent [19]

Imran

[11] Patent Number: 5,389,072
[45] Date of Patent: Feb. 14, 1995

[54] MECHANISM FOR MANIPULATING A TOOL AND FLEXIBLE ELONGATE DEVICE USING THE SAME

[75] Inventor: Mir A. Imran, Palo Alto, Calif.

[73] Assignee: MirCor Biomedical, Inc., Sunnyvale, Calif.

[21] Appl. No.: 893,770

[22] Filed: Jun. 5, 1992

[51] Int. Cl.6 .................... A61M 37/00; F01B 29/10
[52] U.S. Cl. ....................... 604/95; 604/281; 60/527; 606/174
[58] Field of Search .............. 604/95, 281; 606/78, 606/174; 30/228; 148/402; 128/4 S M, 751; 60/527-529

[56] References Cited

U.S. PATENT DOCUMENTS

| | | | |
|---|---|---|---|
| 3,326,207 | 6/1967 | Egan | 128/2.06 |
| 4,509,517 | 4/1985 | Zibelin | 606/127 |
| 4,522,212 | 6/1985 | Gelinas et al. | 128/642 |
| 4,543,090 | 11/1985 | McCoy | 604/95 |
| 4,601,705 | 7/1986 | McCoy | 604/95 |
| 4,649,924 | 3/1987 | Taccardi | 128/642 |
| 4,660,571 | 4/1987 | Hess et al. | 128/784 |
| 4,699,147 | 10/1987 | Chilson et al. | 128/642 |
| 4,715,637 | 12/1987 | Hosoda et al. | 401/39 |
| 4,736,587 | 4/1988 | Suzuki | 60/528 |
| 4,753,223 | 6/1988 | Bremer | 128/4 |
| 4,758,222 | 7/1988 | McCoy | 604/95 |
| 4,776,844 | 10/1988 | Ueda | 604/95 |
| 4,799,474 | 1/1989 | Ueda | 128/4 |
| 4,811,564 | 3/1989 | Palmer | 60/527 |
| 4,841,730 | 6/1989 | McDonald | 60/527 |
| 4,884,557 | 12/1989 | Takehanna et al. | 128/4 |
| 4,900,078 | 2/1990 | Bloch | 294/86.4 |
| 4,921,482 | 5/1990 | Hamerslag et al. | 604/95 |
| 4,940,064 | 7/1990 | Desai | 128/784 |
| 4,944,727 | 7/1990 | McCoy | 604/95 |
| 4,945,912 | 8/1990 | Langberg | 128/642 |
| 4,953,559 | 9/1990 | Salerno | 128/751 |
| 4,954,952 | 9/1990 | Ubhayakar et al. | 901/39 |
| 4,977,886 | 12/1990 | Takehanna et al. | 128/4 |
| 5,010,894 | 4/1991 | Edhag | 128/785 |
| 5,020,842 | 6/1991 | Miwa et al. | 901/31 |
| 5,037,391 | 8/1991 | Hammerslag et al. | 604/95 |
| 5,078,684 | 1/1992 | Yasuda | 604/95 |
| 5,219,357 | 6/1993 | Honkanen et al. | 128/751 |
| 5,236,424 | 8/1993 | Imran | 604/264 |
| 5,238,002 | 8/1993 | Devlin | 128/751 |

FOREIGN PATENT DOCUMENTS 2163055  8/1985  United Kingdom ........... A61B 5/04

Primary Examiner—C. Fred Rosenbaum
Assistant Examiner—Mark Bockelman
Attorney, Agent, or Firm—Flehr, Hohbach, Test, Albritton & Herbert

[57] ABSTRACT

Flexible elongate device comprising a flexible elongate member having proximal and distal extremities and a tool actuator member mounted on the distal extremity of the flexible elongate member. An elongate element having a negative coefficient of expansion is carried by the distal extremity of the flexible elongate member and is connected to the tool actuator member for causing movement of the tool actuating member. A control console is provided for supplying electrical energy to the elongate element.

21 Claims, 4 Drawing Sheets

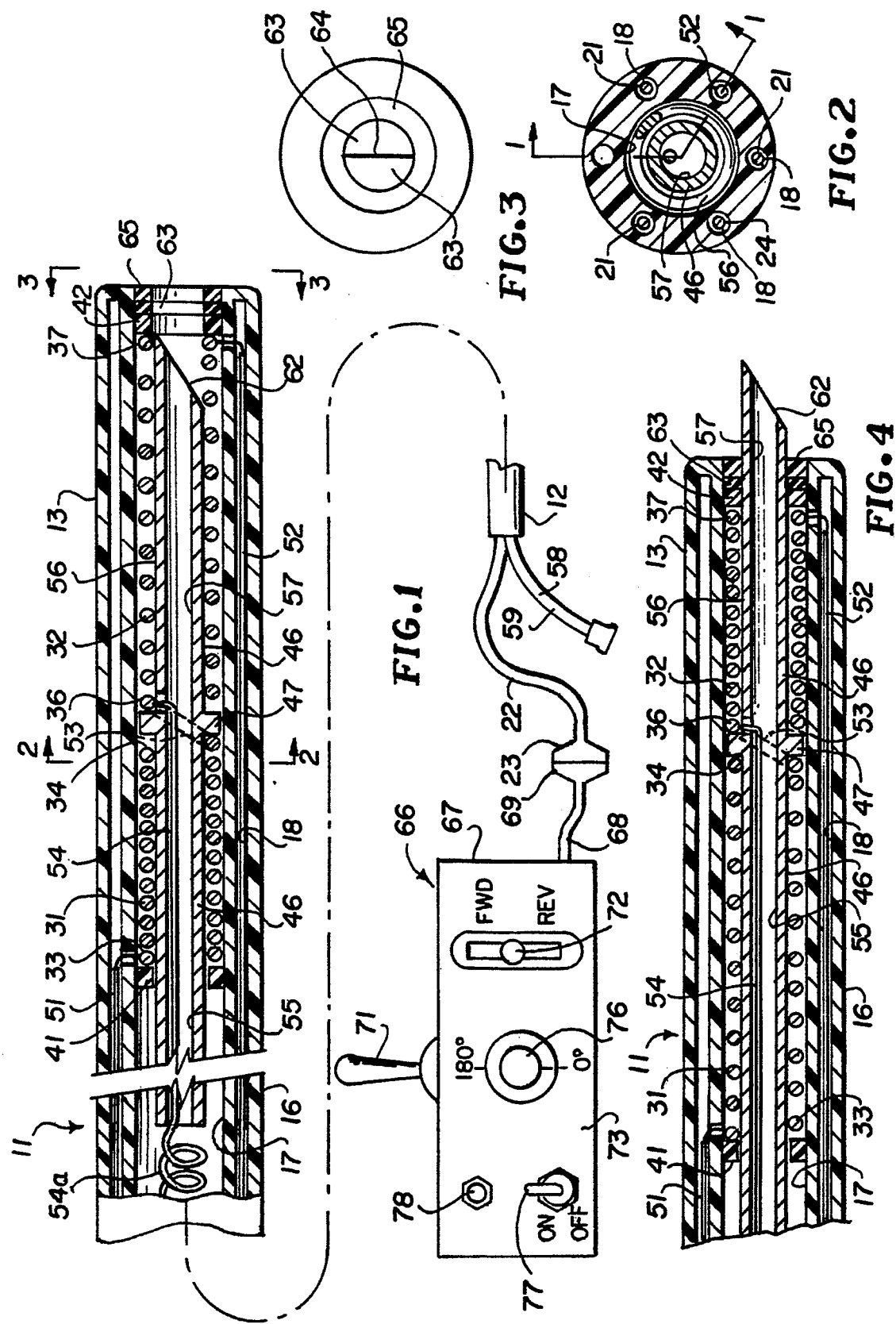

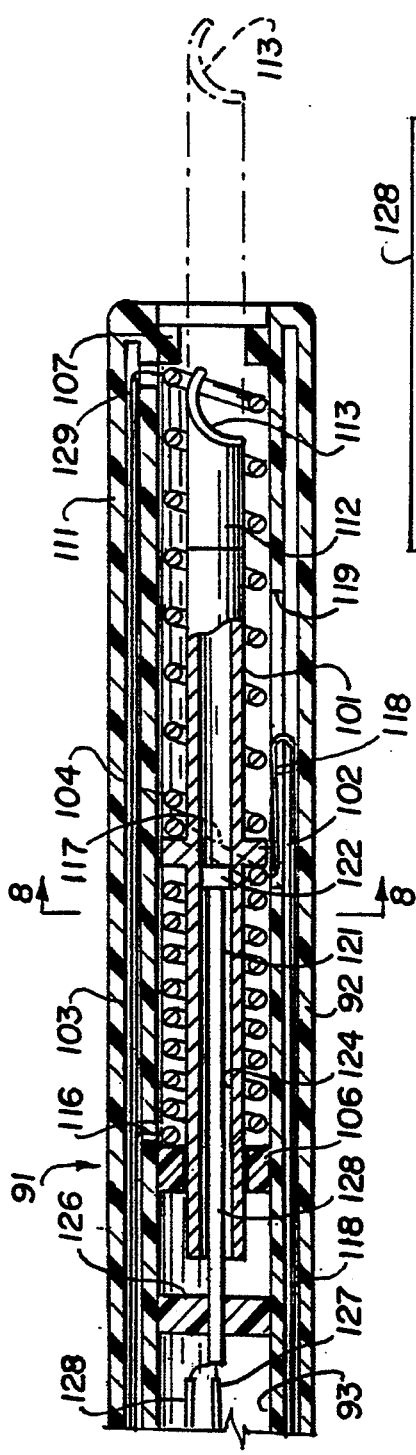
FIG.7
FIG.8
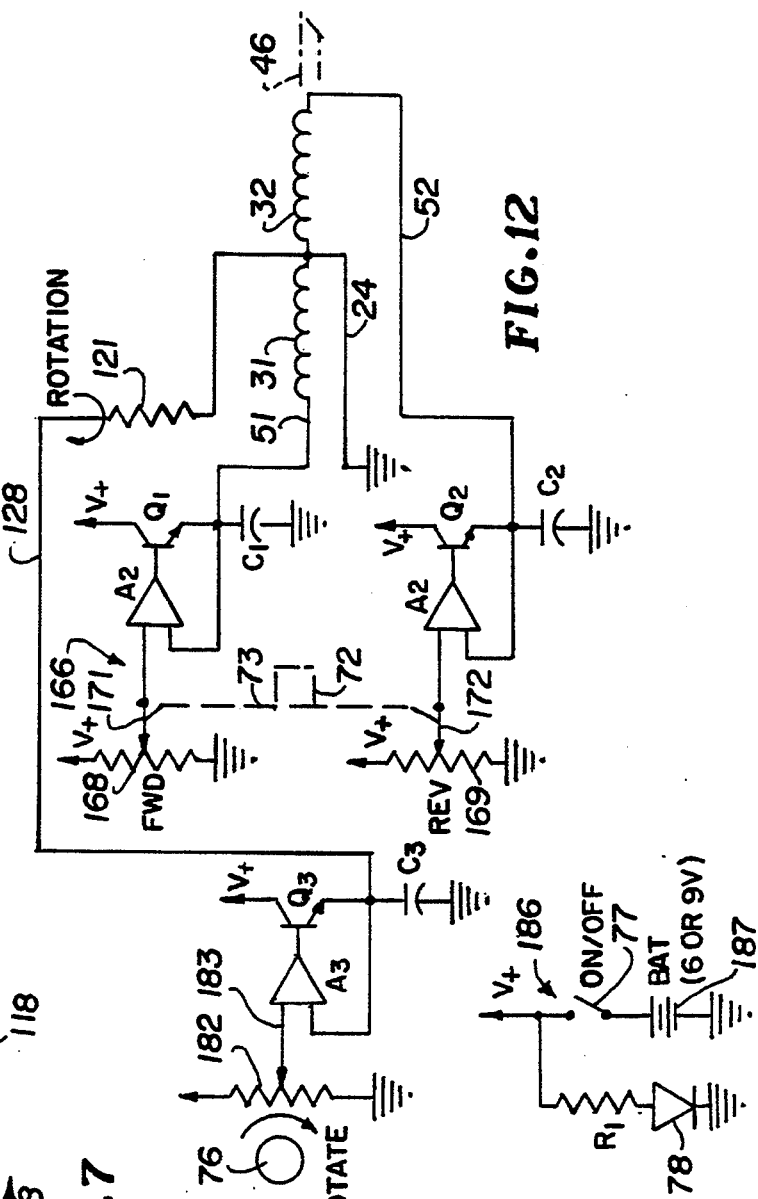
FIG.12

MECHANISM FOR MANIPULATING A TOOL AND FLEXIBLE ELONGATE DEVICE USING THE SAME

This invention relates to a mechanism for manipulating a tool and to a flexible elongate device using the same.

In many medical procedures, particularly those utilizing guidewires and catheters and other minimally invasive surgical procedures, it has been desirable to perform certain physical operations at the distal extremities of the same. This has been difficult to accomplish. In certain applications, pull wires or levers have been utilized to perform operations at the distal extremities. However, they have serious limitations because of the frictional engagement between the pull wires and the device in which they are operating. Also, they have been unsatisfactory because they provide at best a slow response. There is therefore a need for a new and improved mechanism for manipulating a tool at the distal extremity of a flexible elongate device, and particularly for small diameter guidewires and catheters.

In general, it is an object of the present invention to provide a mechanism for manipulating a tool.

Another object of the invention is to provide a mechanism of the above character which can be very small and can be provided at the distal extremities of flexible elongate devices.

Another object of the invention is to provide a mechanism of the above character which has a fast response.

Another object of the invention is to provide a mechanism of the above character in which a rectilinear motion can be provided.

Another object of the invention is to provide a mechanism of the above character in which the rectilinear motion can be converted into circular motion.

Another object of the invention is to provide a mechanism of the above character which can be readily controlled.

Another object of the invention is to provide a mechanism of the above character which can be utilized with a flexible elongate device having a steerable distal extremity.

Another object of the invention is to provide a mechanism of the above character in which a fluid can be introduced through the distal extremity of the flexible elongate device.

Another object of the invention is to provide a flexible elongate device incorporating the mechanism for manipulation of a tool which permits the use of a relatively small diameter for the flexible elongate device.

Another object of the invention is to provide a mechanism of the above character which can be utilized with various types of tools utilized in medical procedures.

Additional objects and features of the invention will appear from the following description in which the preferred embodiments are set forth in detail in conjunction with the accompanying drawings.

FIG. 1 is a side elevational view partially in cross-section of a flexible elongate device having mounted on the distal extremity thereof a mechanism for manipulating a tool incorporating the present invention and the control console for use therewith and showing the tool in a retracted position.

FIG. 2 is a cross-sectional view taken along the line 2—2 of FIG. 1.

FIG. 3 is a end elevated view taken along the line 3—3 of FIG. 1.

FIG. 4 is a cross-sectional view similar to FIG. 1 showing the tool in extended position.

FIG. 7 is a side-elevational view of a flexible elongate device having a mechanism mounted on the distal extremity thereof showing another embodiment of the present invention which is utilized for manipulating a tool with rotational rectilinear motion.

FIG. 8 is a cross-sectional view taken along the line 8—8 of FIG. 7.

FIG. 12 is a circuit diagram showing a portion of the circuitry utilized in the control console shown in FIG. 1.

Figure 5:
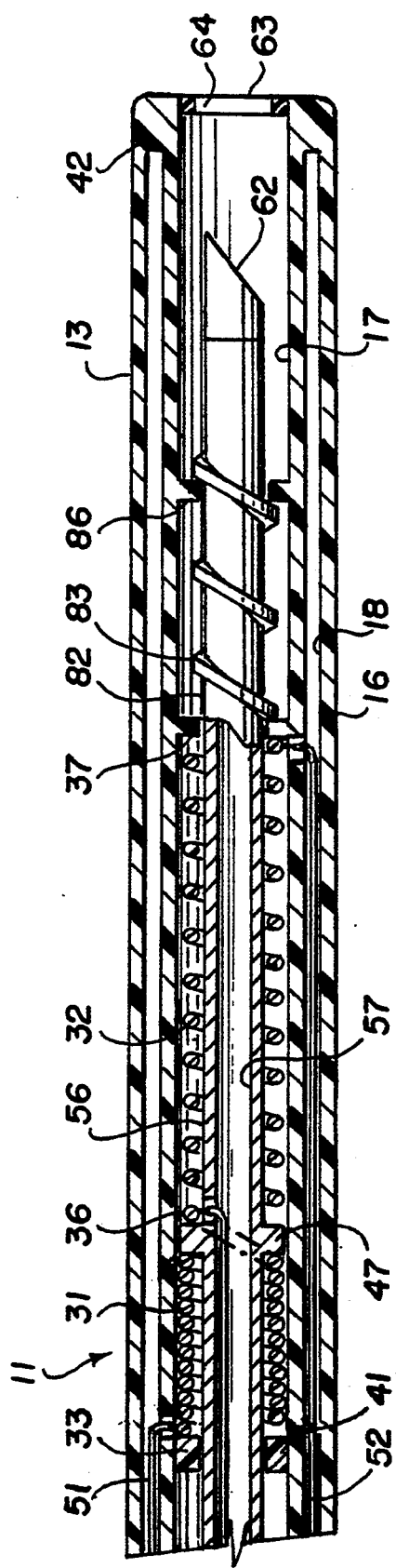
FIG. 5 is a side-elevational view partially in cross-section of the distal extremity of another flexible elongate device having a mechanism mounted on the distal extremity thereof incorporating the present invention for manipulating a tool to provide rotatable motion to the tool and showing the tool in a retractable position.

In general, the mechanism for manipulating a tool which is adapted to be mounted on the distal extremity of a flexible elongate device is comprised of a housing. A tool actuating member is provided in the housing. First and second springs formed of a shape memory material are disposed in the housing. Each of the springs has first and second ends. Means is carried by the housing engaging the first end of the first spring and engaging the second end of the second spring. Means is also carried by the tool actuating member and is engaged by the second end of the first spring and the first end of the second spring. Means is provided for supplying current to the first and second springs for causing movement of the tool actuating member. This movement is a rectilinear movement which can be converted to rotational movement.

More specifically, as shown in FIGS. 1 and 2 of the drawings, a flexible elongate device 11 in the form of a catheter is provided. The flexible elongate device 11 has proximal and distal extremities 12 and 13. The flexible elongate device 11 consists of a flexible elongate member 16 formed of a suitable medical grade plastic such as polyethylene, polyamide or a silicone. As shown in FIG. 2, it can be cylindrical in form and is provided with a centrally disposed lumen 17 which extends from the proximal extremity 12 to the distal extremity 13 of the device 11. It is also provided with a plurality of smaller lumens 18 which are circumferentially spaced around the central lumen 17. For example, six of such lumens 18 can be provided which are equally spaced around the central lumen 17. The lumens 18 extend from the proximal to the distal extremities 12 and 13 of the flexible elongate device and can be utilized for various purposes. Three of the lumens 18 can be utilized for steering wires 21 of the type described in co-pending application Ser. No. 07/793,858 now U.S. Pat. No.

5,238,005, filed on Nov. 18, 1991, for causing steering movement of the distal extremity of the flexible elongate device 11. As described in said co-pending application, the steering wires 21 are formed of a material having a negative coefficient of expansion and are formed of a suitable material such as a nickel-titanium alloy manufactured and sold under the trademark Flexinol by Toki of Japan.

As also described in said co-pending application, the steering wires 21 are connected to electrical conductors (not shown) which extend through a cable 22 at the proximal extremity 12 of the catheter 11 and are connected to an electrical connector 23 and are adapted to be connected to a controller of the type described is said co-pending application. The distal extremities of the steering wires 21 are secured to the distal extremity of the flexible elongate member 16 in a suitable manner such as by bonding the distal extremities of the wires in the distal extremities of the lumens 18 by an adhesive so that they are retained therein. The three steering wires 21 are offset by a suitable angle, as for example 120° from each other, to provide the desired motion of the distal extremity of the device 11.

First and second coil springs 31 and 32 are disposed within the central lumen 17 near the distal extremity thereof as shown in FIG. 1. The helical coil springs 31 and 32 are formed of a shape memory material such as Nitinol. The springs are fabricated in the following manner: The Nitinol wire of appropriate diameter (such as 0.005") is wound on a mandrel having a spiral groove. The pitch of the spiral groove determines the pitch of the spring when actuated (expanded). The two ends of the Nitinol wire are secured (with set screws) and heated at 400° C. to 550° C. for 10-15 minutes to provide the shape memory. The transition temperature is chosen above body temp (of 45° C.) so that the Nitinol springs can only be activated by the application of electricity. The spring 31 is provided with a first or proximal end 33 and a second or distal end 34 and, similarly, the spring 32 is provided with a first or proximal end 36 and a second or distal end 37. The springs can be formed of a wire of various diameters. For example, the springs can be formed of wire having a diameter to provide the desired force, as for example, from 0.001" to 0.020" and preferably a diameter of 0.004". Such wire can be utilized to form coils of various outside diameters ranging from 0.010" to 0.1", and having inside diameters ranging from 0.008 to 0.080". The springs 31 and 32 can be formed of the same length or can be formed of different lengths ranging from ¼" to 2". The length of the springs is dependent on the desired motion to be provided by the springs.

The distal extremity of the flexible elongate member 16 serves as a housing for the springs 31 and 32 disposed within the central lumen 17. Means is carried by the flexible elongate member serving as the housing for engaging the first or proximal end of the first spring and the distal or second end of the second spring, and consists of an annular member or ring 41 which is mounted in the lumen 17 and is secured to the side wall of the flexible elongate member or housing 16 by suitable means such as an adhesive (not shown). This ring 41 engages the proximal extremity of the first spring 31.

Similarly, another annular member or ring 42 is mounted within the lumen 17 and is secured to the side wall of the flexible elongate member 16 forming the lumens 17 by suitable means such as an adhesive (not shown). This ring 42 is engaged by the distal or second extremity of the second spring 32.

A tool actuating member 46 is disposed within the central lumen 17 and within the coil springs 31 and 32. This tool actuator member 46 as shown in FIG. 2 is cylindrical in cross-section and forms a part of a cannula which is used as hereinafter described. The tool actuating member 46 is formed of a suitable material such as stainless steel. Means is provided which is carried by the tool actuating member 46 which is adapted to be engaged by the second or distal extremity of the first spring 31 and the first or proximal extremity of the second spring 32, and consists of a annular flange 47 formed integral with the tool actuating member 46 which is engaged by the second or distal extremity of the first spring 31 and by the proximal or first end of the second spring 32.

Means is provided for supplying electrical energy to the first and second springs 31 and 32, and consists of insulated conductors 51 and 52 which are provided in two of the lumens 18. The conductor 51 is connected to the distal extremity of the first coil spring 31. Similarly, the conductor 52 is connected to the distal extremity of the second spring 32. The distal extremity of the spring 31 and the proximal extremity of the spring 32 are interconnected by a cross link 53 extending through a hole (not shown) in the flanges 47. The cross link 53 is connected by an insulated conductor 54 also extending through a hole (not shown) in the tool actuator member 46 and passing proximally interiorally of the tool actuator member through a bore 55 and connected to the common return conductor 24. The conductor 54 is provided with a coiled portion 54a to accommodate the rectilinear movement of the tool actuator member 46 as hereinafter described. These additional conductors 51 and 52 also extend through the cable 22 and are connected to the conductor 23 so that electrical energy can be supplied to the same for supplying energy to the springs 31 and 32.

As explained previously, the tool actuator member 46 is adapted to be secured to a tool 56 which is shown in the form of a cannula. The tool cannula 56 is circular in cross-section and is provided with a flow passage 57 which adjoins the bore 55. As shown in FIG. 1, and the tool actuating member 46 and the cannula 56 are formed as a single integral member. However, it should be appreciated that they can be formed of two separate members which can be joined together in a suitable manner, such as by brazing. As shown, the flow passage 57 is in communication with the bore 55 in the tool actuator member 56 and opens into the central lumen 17. The central lumen 17 at the proximal extremity of the flexible elongate member 16 is connected to a flexible elongate member 58 in a suitable manner such as by an adhesive which also is provided with a flow passage 59 in communication with the central lumen 17 which is connected to a Luer adapter 61 which is adapted to be connected to a conventional syringe (not shown) whereby a liquid can be supplied to the member 58 and through the flow passage 57 provided in the cannula 56. The cannula 56 is provided with an inclined circular sharpened edge 62 which is adapted to extend through a disk-type valve member 63 which is provided with a diametrically extending slit 64 (see FIG. 3). The valve member 63 is retained in place by ring 65.

A control console 66 is provided for controlling the flexible elongate device 11. The control console is provided with a cabinet 67 with a cable 68 extending there-from and having a female connector 69 mounted thereon which is adapted to receive the male connector 23 connected to the cable 22 of the flexible elongate device 11. A joystick 71 is mounted on the top of the cabinet 66 as shown in FIG. 1 which is movable throughout 360° of a cone to control the steering wires 21 in a manner described in co-pending application Ser. No. 793,858 filed on Nov. 18, 1991. The joystick 71 operates circuitry of the type disclosed in said co-pending application, which is incorporated in the cabinet 67. It also includes circuitry of the type shown in FIG. 12 hereinafter described. A sliding mechanism 72 is provided on the front wall 73 of the cabinet 67, movable between forward and reverse positions. It also includes a control knob 76 mounted on the front wall 73, rotatable between 0° and 360°. It also includes an on-off switch 77 and a light-emitting diode 78 to indicate when the power is on. The control console 66 is connected to a suitable source of power such as 110 volts AC, or alternatively it can be provided with battery power.

The control console 66 is utilized to cause linear motion by forward and reverse motion of the cannula or tool 56 by causing it to pass through the slit 64 in the valve member 63 to perform surgical operations. The valve member 63 serves to prevent blood from coming back into the catheter or flexible elongate device 11.

In certain applications, it is desirable to translate the rectilinear motion hereinbefore described into rotational or circular motion. This can be accomplished with the flexible elongate device shown in FIG. 5. This flexible elongate device 81 is similar in many respects to the flexible elongate device 11, with the exception that the cannula tool 56 provided in flexible elongate device 11 has been elongated to provide an elongated tool or cannula 82.

Cooperative means is provided between the distal extremity of the cannula 82 and the distal extremity of the flexible elongate member 16 for translating rectilinear motion into rotary motion and, as shown, consists of helical ribbon or structure 83 which can be formed integral with the cannula 82 or, alternatively, can be formed as a separate part bonded to the exterior of the cannula 82 by suitable means such as brazing. The helical structure 83 provides an annular helical groove 84 which is inclined at a suitable angle, as for example 60°. Means is provided for engaging the helical structure 83 and consists of an annular protrusion 86 formed of a suitable material such as a metal or plastic which is secured to the interior wall of the flexible elongate member 16 forming the lumen 17 by suitable means such as an adhesive. Thus it can be seen, the protrusion 86 is seated within the groove 84. With such a construction, it can be readily appreciated that as the cannula or tool 82 is advanced or retracted as hereinafter described, the cannula tool 82 will also be rotated as it is advanced or retracted.

The protrusion 86 can form a single thread extending outwardly from the interior surface forming the lumen 17. It should be appreciated that many different types of mechanisms can be provided for translating the linear motion into simultaneous rotary motion. For example, helical grooves could be provided in the interior surface of the flexible elongate member 16 with corresponding grooves being provided in the exterior surface of the cannula with low-friction interengaging means such as a pin or a ball seated in the grooves to cause rotary motion upon linear translation of the cannula or tool.

When it is desired to encounter less friction to obtain rotational movement as the tool is translated linearly, this can be accomplished in an embodiment of the invention such as shown in FIGS. 7 and 8. A flexible elongate device 91 is provided which consists of a flexible elongate member 92 of the same type as the flexible elongate member 16. It has a centrally disposed lumen 93 which extends longitudinally thereof. The flexible elongate member 92 is provided with a plurality of additional lumens 94 which are spaced apart circumferentially around a large central lumen 93 as shown in FIG. 8. Three steering wires 96 are provided in the lumens 94 and are spaced approximately 120° and are fastened in the distal extremities of the lumens 94 in the manner hereinbefore described with the embodiment of the invention shown in FIGS. 1 and 2. The steering wires 96 are connected to a common return conductor 97 (see FIG. 8).

A tool 101 in the form of a cannula is provided in the distal extremity of the flexible elongate member 92 and is disposed in the lumen 93. The tool or cannula 101 is provided with a radially extending flange 102 between the ends of the same, which is engaged by the distal extremity of first spring 103 and by the proximal extremity of a second spring 104 coaxially disposed on the tool or cannula 101 as shown in FIG. 7. The first and second springs 103 and 104 are formed of the Nitinol material hereinbefore described for the springs 31 and 32. The proximal extremity of the first spring 103 engages an annular flange 106 adhered to the inner surface forming the lumen 93 by suitable means such as an adhesive, and the distal extremity of the second spring 104 engages a similar annular flange 107 secured to the interior surface forming the lumen 93. An attachment 111 is secured to the distal extremity of the tool or cannula 101 by suitable means such as a fitting 112. The attachment 111 is provided with an arcuate or substantially semicircular cutting edge 113.

The first spring 103 has one or the other proximal end connected to a conductor 116. The other or distal end connected to the proximal end of the second spring 104 by a cross link 117 extending through a hole (not shown) in the flange 102 and connected to a conductor 118 that is connected to elongate alot 119. The conductor 118 is connected to the common return conductor 97. Similarly, a conductor 120 is connected to the distal end of the second spring 104 which has its other end connected to the common return conductor 97. These electrical connections are utilized to cause rectilinear motion of the tool or cannula 101 in the manner hereinbefore described.

Additional means is provided in the flexible elongate device 91 to provide rotational movement independent of the rectilinear motion of the tool or cannula 101. A Nitinol wire 121 has programmed into its memory rotational motion. This is accomplished by first taking a piece of Nitinol wire and clamping one end of the same, and then rotating the other free end by the desired number of turns, and then clamping the wire into another clamp to hold it in this rotated position. The Nitinol wire thus clamped is then heated to an appropriate annealing temperature such as 500° to 550° C. for a period of time ranging typically from 4 to 6 minutes to thereby incorporate the turns into its memory. Thereafter the Nitinol wire 121 is permitted to cool to room temperature. One end of the wire 121 is secured to a block 122 by suitable means such as by spot welding. The block 122 is slidably mounted within the tool or cannula 101. Cooperative means is provided between the block and the cannula for causing rotational movement of the cannula as the block 122 is rotated. Thus, as shown particularly in FIGS. 4 and 5, the block 122 is rectangular in shape and cooperates with the rectangular bore 124 provided within the tool or cannula 101, which has the same general configuration as the block 122.

It should be appreciated that many different alternatives for the cooperating means can be utilized. For example, an oval-shape could be utilized and a key and keyway could be provided. All that is necessary is the connection which permits rectilinear movement of the tool or cannula 101 and at the same time permits rotational movement to be independently applied to the tool or cannula.

The other end of the wire 121 is secured to another block 126 which is mounted in a fixed position in the lumen 93 by suitable means such as by an adhesive. The block 126 is provided with a bore 127 into which the proximal extremity of the Nitinol wire 121 extends and is bonded therein by suitable means such as by spot welding.

Means is provided for supplying electrical energy to the Nitinol wire 121 and consists of insulated conductors 128 and 129 connected to the proximal end of the wire 121 and conductor 129 extending through a bore 130 in the wire 121 and being connected to the distal extremity of the wire 121.

This additional insulated conductor 129, for example, can extend through bore 131 provided in the wire 121 extending to the distal extremity of the wire 121. The conductor 129 can then be connected to the common return 97.

The conductors to the steering wires 96 and the other conductors provided in the lumens 94 are brought out to the proximal extremity of the flexible elongate device 91 and are connected to a control console 66 of the type hereinbefore described. The operation of the device 81 in conjunction with the control console will hereinafter be described in conjunction with the circuit diagram in FIG. 12.

Figure 9:
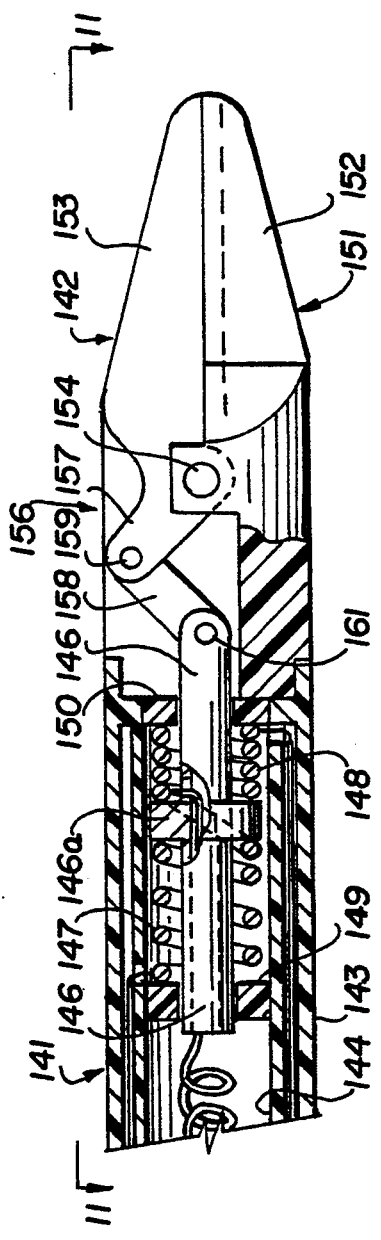
FIG. 9 is a side elevational view of the distal extremity of a flexible elongate device having a mechanism for manipulating a tool mounted on the distal extremity thereof incorporating another embodiment of the invention for providing a scissors which is shown in a closed position.
Figure 10:
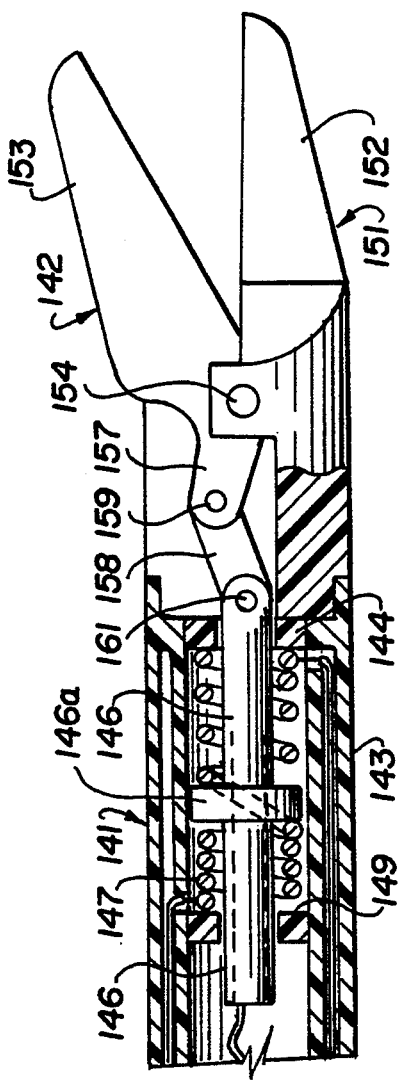
FIG. 10 is a view similar to FIG. 9 showing the scissors in an open position.
Figure 11:
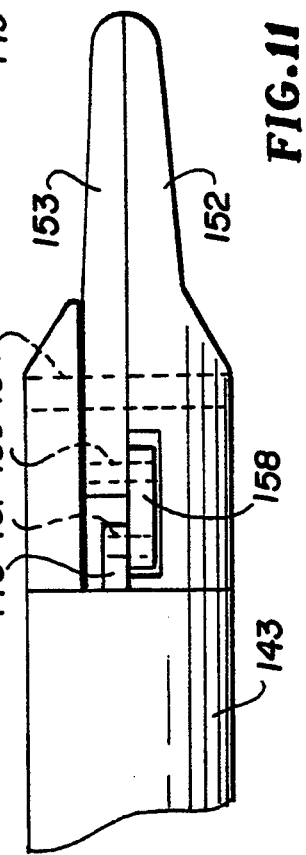
FIG. 11 is a top plan view looking along the line 11—11 of FIG. 9.

Another embodiment of the invention is shown in FIG. 9–11, in which rectilinear movement is converted into a clamping or scissors-like action. The flexible elongate device 141 shown in FIG. 8 is provided with a tool 142 on its distal extremity. As in the previous embodiments of the present invention, the flexible elongate device 141 consists of a flexible elongate member 143 which has a lumen 144 extending therethrough. A tool actuator member 146 of the type hereinbefore described in slidably mounted for rectilinear movement within the lumen 144. The actuator member 146 is move rectilinearly by the use of Nitinol springs of the type hereinbefore described and electrically energized in the manner hereinbefore described, which includes the first and second Nitinol springs 147 and 148 engaging annular circular abutments 149 and 150 provided in the lumen 144 and a centrally disposed flange portion 146a on the tool actuator member 146.

A scissor mechanism 151 is mounted in the distal extremity of the tubular member 143 and consists of a first cutting blade 152 having pivotally connected thereto another cutting blade 153 by pivot pin 154. A linkage 156 is provided for interconnecting the distal extremity of the tool actuator member 146 to the movable blade 153 and consists of a link 157 which has one end mounted in a fixed position on the blade 153 and has the other end pivotally connected to one end of a link 158 by a pin 159. The other end of the link 158 is pivotally connected by a pin 161 to the distal extremity of the tool actuator member 146. It can be seen that by the linkage provided, the rectilinear movement of the tool actuator member 146 will cause closing and opening of the movable blade 153 with respect to the fixed blade 152 to perform a cutting action as shown in FIG. 9. Also it should be appreciated that the scissors can be moved to a closed position as shown in FIG. 9 so that it will not damage tissue as the flexible elongate device or catheter is being introduced in a vessel.

Figure 6:
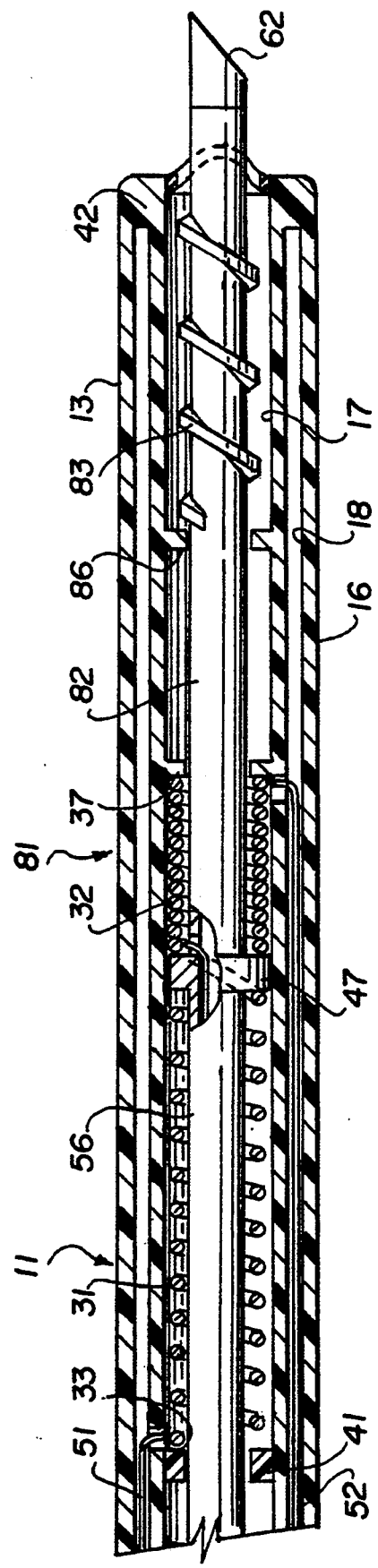
FIG. 6 is a cross-sectional view similar to FIG. 5 but showing the tool in an advanced position.

Operation of the various flexible elongate devices 11, 81 and 141 hereinbefore described may now be considered in connection with the circuitry as shown in FIG. 12. This circuitry is disposed within the control console 66. FIG. 11 shows the Nitinol springs which are utilized in the present invention. For the embodiments shown in FIGS. 1 and 2, the springs are 31 and 32. The same is true for the embodiment shown in FIGS. 5 and 6. In FIG. 7, the springs would be respectively springs 103 and 104, and in the embodiment shown in FIG. 9, the springs would be spring 147 and 148. However, it should be appreciated that the other springs for providing rectilinear movement in the other embodiments could be substituted for the springs 31 and 32.

The two springs 31 and 32 are energized by two variable power supplies 166 and 167. The power supplies 166 and 167 include potentiometers 168 and 169 which are provided with wiper arms 171 and 172 that are ganged together as shown by the dotted line 173 and connected to the slide mechanism 72 of the control console 66. In each of the power supplies 166 and 167, the wiper arms 171 and 172 are connected to the inputs of amplifiers A1 and A2, respectively, to provided currents to the transistors Q1 and Q2 which create voltages on their outputs which correspond to the inputs from the wiper arms 171 and 172. Capacitors C1 and C2 are provided to filter the outputs. These outputs are utilized to supply current through the conductors 51 and 52 to the Nitinol springs 31 and 32. This current passes through the same, and then returns to ground through the common conductor 24. By way of example, if it is desired to advance the tool actuator member 46 in the forward direction, the slider 72 is advanced upwardly on the front panel 73 of the control console 66. This causes current to be supplied through the conductor 51 to the Nitinol spring 31 to cause the same to expand with the electrical energy supplied to the same to move the tool actuator member 46 forward. If still further advancement of the tool 46 is required, the physician can move the slider 72 still further upwardly to cause still further advancement of the tool. When it is desired to retract the tool, it is merely necessary to move the slider 72 downwardly on the front panel 73, which causes energy to be supplied through the conductor 52 to the Nitinol spring 32 to cause it to expand and to cause the tool actuator member 46 to be moved to the rear or in reverse. Thus, it can be seen that it is possible to readily achieve rectilinear movement of the tool actuator member in a very small confined space. A catheter incorporating the present invention can be made of any desired size. However, the present invention particularly lends itself to small-diameter devices, as for example 7 French and below, or, in other words, devices having diameters ranging from 0.040 to 0.100".

The catheters can have any suitable length, as for example ranging from 150 to 200 cm depending upon the application. The proximal extremity can be steered so that the tool which is being operated can be properly positioned in the manner described in co-pending application Ser. No. 07/793,858 filed on Nov. 18, 1991 now U.S. Pat. No. 5,238,005, by operation of the joystick 71.

In connection with the embodiments shown in FIG. 4, the rectilinear motion of the tool actuator member can also be caused to rotate by operation of the slider 72. However, as previously pointed out, this rotational movement is dependent upon the rectilinear motion of the tool actuator member.

When independent rotational movement is desired, a construction of the type shown in FIGS. 7 and 8 is utilized, which requires the use of additional circuitry shown in FIG. 7. This additional circuitry takes the form of an additional power supply 181 which is provided with a potentiometer 182 having a wiper arm 183. Current from the wiper arm is supplied to the input of an amplifier 83 which amplifies the current and supplies it to a transistor Q3 which has its output filtered by capacitor C3. The output is supplied through the conductor 128 to the Nitinol wire 121. The wiper 183 is controlled by the knob 76 provided on the front panel 73. As the knob 76 is rotated, current is supplied through the conductor 128 to the wire 121 which, because of the memory incorporated therein, causes rotation of one end of the wire with respect to the other end of the wire, as for example by causing rotation of the block 122 which will cause a rotation of the tool actuator member 101. The amount of rotation of the tool actuator member 101 can be controlled by the rotational position of the knob 76. By rotating the knob 76 in the opposite direction, the block 122 can be caused to rotate in an opposite direction carrying with it in rotational movement to tool actuator member 101. In this connection it should be appreciated that during the time this rotational movement is occurring, independent rectilinear movement of the tool 101 can be accomplished by operating the slider 72. Also, independently or simultaneously, the position of the distal extremity of the flexible elongate device can be steered or positioned by controlling the joystick 71.

From the foregoing it can be seen that there has been provided a flexible elongate device 11 which has a tool carried by the distal extremity thereof which is capable of a multiplicity of operations. For example, the tool carried by the tool actuator member can be advanced and retracted rectilinearly and can also be caused to rotate either independently or in conjunction with the rectilinear movement.

At the same time or independently, the distal extremity of the flexible elongate device which typically is in the form of a catheter, can be moved in various desired positions by the use of the joystick. All of these operations can be performed simultaneously or individually, depending upon the desires of the operator.

A power supply for providing the V+ voltages shown in the circuitry is provided from a battery 187 through the on-off switch 77 and mounted on the front panel. When the switch is in the "ON" position, power is supplied through a resistor R1 to the LED 78 provided on the front panel 73. The battery 187 can be of a suitable voltage, such as 6 or 9 volts.

What is claimed is:

1. A flexible elongate device in the form of a small diameter guide wire or catheter for entering a vessel of a human body comprising a flexible elongate member having proximal and distal extremities, a tool actuator member mounted in the distal extremity of the flexible elongate tubular member, actuator element means having a negative coefficient of expansion disposed within the distal extremity of the flexible elongate member, said actuator element means including first and second opposing heat actuatable actuator elements said actuator element means having a transition temperature which is above the body temperature, electrical control means at the proximal extremity for supplying electrical energy to the actuator element means and means coupling the actuator elements to the tool actuator member for causing movement of the tool actuator member and to cause operation of the operable tool when heat is supplied to the actuator element means.

2. A device as in claim 1 wherein said actuator element means and the coupling means are constructed to supply linear motion to the tool actuator member when heat is supplied to the actuator element means.

3. A device as in claim 2 wherein the tool actuator member includes means carried thereby for providing movement in directions which are offset with respect to the longitudinal axis of the flexible elongate member.

4. A device as in claim 1 wherein said actuator element means includes first and second springs whereby when electrical energy is supplied to the first spring, the tool actuator member is moved in one direction and when electrical energy is supplied to the second spring the tool actuator member is moved in an opposite direction.

5. A device as in claim 4 wherein the coupling means includes a flange secured to a cylindrical tool actuator member and wherein said tool actuator member is cylindrical in form and has said first and second springs coaxially mounted thereon.

6. A device as in claim 1 wherein said actuator element means and the coupling means are constructed to supply rotational movement to the tool actuator member when heat is supplied to the actuator element means.

7. A device as in claim 3 wherein the actuator element means and the coupling means includes cooperative means in the form of a helical structure and an annular protrusion carried by the tool actuator member and the flexible elongate member for imparting rotational movement to the tool actuator member as the tool actuator member is moved rectilinearly.

8. A device as in claim 6 together with means for providing rectilinear motion of the tool actuator member independent of rotation of the tool actuator member.

9. A device as in claim 1 wherein said actuator element means includes an elongate element having first and second ends, means securing the first end within the flexible elongate member to prevent rotation thereof, means securing the second end of the elongate element to the tool actuator member to permit rectilinear movement of the tool actuator member but preventing rotation of the tool actuator member with respect to the second end of the elongate element whereby as the second end of the elongate element is rotated, the tool actuator member is rotated.

10. A device as in claim 1 including a tool wherein said tool is in the form of first and second members movable towards and away from each other and a linkage connecting at least one of said first and second members to said tool actuator member for causing movement of said first and second members toward and away from each other.

11. A device as in claim 1 together with valve means carried by the distal extremity of the flexible elongate member and being movable between open and closed positions to permit a tool to pass therethrough so that when a tool is advanced therethrough liquid is prevented from entering the distal extremity of the flexible elongate device and when a tool is retracted so that the tool no longer extends through the valve member the valve member closes.

12. A device as in claim 1 wherein said tool is provided with a flow passage extending therethrough and wherein said tool actuator member includes means for providing a flow passage in communication with the flow passage in the tool.

13. A device as in claim 1 wherein said flexible elongate member has a diameter of 7 French or less.

14. A mechanism for use in the medical field for manipulating a tool carried by the distal extremity of a flexible elongate tubular member having proximal and distal extremities and having a lumen therein extending from the proximal to the distal extremities and being adapted to be inserted into a vessel of a human body, comprising a tool actuator member disposed in said lumen and adapted to be connected to said tool, and actuation element means having a negative coefficient of expansion, said actuation element means including first and second opposing heat actuator elements having a transition temperature which is above the body temperature, means coupling the actuation element means to the tool actuator member and electrical means for supplying electrical energy to heat the actuation element means to cause motion to be supplied to tool actuator member to cause it to move in said lumen.

15. A mechanism as in claim 14 together with a console connected to the proximal extremity of the flexible elongate tubular member, said control console having manually controlled means for controlling the electrical means for causing the movement of the tool actuator member in said lumen.

16. A mechanism as in claim 15 wherein the coupling means is constructed to cause rectilinear movement of the tool actuator member in said lumen when the actuation element means is heated above body temperature.

17. A mechanism as in claim 16 wherein the coupling means includes means for translating rectilinear movement to rotational movement of the tool actuator member.

18. A mechanism as in claim 17 wherein the coupling means includes means for causing rotational movement of the tool actuator member independent of rectilinear of the tool actuator member.

19. A mechanism as in claim 15 wherein the coupling means is constructed to cause rotational movement of the tool actuator member in said lumen when the actuation element means is heated above body temperature.

20. A mechanism as in claim 15 wherein said flexible elongate tubular member has a longitudinal axis together with electrical means connected to the distal extremity of the flexible elongate tubular member for causing movement offset from the longitudinal axis of the elongate tubular member and extending through 360° for steering the distal extremity of the flexible elongate member.

21. A mechanism as in claim 14 wherein said flexible elongate member has a diameter of 7 French or less.

* * * * *